United States Patent [19]
Spaulding et al.

[11] Patent Number: 5,551,319
[45] Date of Patent: Sep. 3, 1996

[54] DEVICE FOR MARKING AND ARTICLE WITH INK

[75] Inventors: Darwin Spaulding, Voorheesville; Andrew J. Stanton; Byron Fleury, both of St. James, all of N.Y.

[73] Assignee: Spaulding & Rogers Mfg., Inc., Voorheesville, N.Y.

[21] Appl. No.: 470,068

[22] Filed: Jun. 6, 1995

[51] Int. Cl.$^6$ ................................................ B43K 5/00
[52] U.S. Cl. ........................................ 81/9.22; 30/362
[58] Field of Search .............................. 81/9.22; 30/362, 30/366; 606/116, 185

[56] References Cited

U.S. PATENT DOCUMENTS

| 768,413 | 8/1904 | Wagner | 606/116 |
|---|---|---|---|
| 3,933,104 | 1/1976 | Kelly . | |
| 4,204,438 | 5/1980 | Binaris et al. | 81/9.22 |

FOREIGN PATENT DOCUMENTS

| 1587519 | 4/1981 | United Kingdom | 81/9.22 |
|---|---|---|---|

Primary Examiner—D. S. Meislin
Assistant Examiner—Joni Danganan
Attorney, Agent, or Firm—McGlew and Tuttle, P.C.

[57] ABSTRACT

A marking device with a reciprocating needle. The needle is attached to an armature which reciprocates in a slot in a housing by a crank which is rotated by a motor in the housing. Vibration of the motor and tolerances between the armature and track cause unwanted movements of the needle in a plane perpendicular to the reciprocating motion. Guide bars and bushings connect the armature to the track. Tolerances between the guide bars and bushings are less than tolerances between the armature and track. An armature bracket is detachably connected to the housing in order to partially or fully close off an open end of the track after the armature has been inserted into the track. Guide bars and bushings then connect the armature and the armature bracket. The motor is supported on only one end by bolts extending from a mounting wall inside the housing. A damping plate is positioned between the motor and the mounting wall, and a damping ring is positioned between, and contacts, the damping ring and the housing. The damping ring is made of material to absorb or block vibrations. Undesirable movements due to a vibration of the motor and tolerances between the armature and the housing are thus removed.

24 Claims, 5 Drawing Sheets

DEVICE FOR MARKING AND ARTICLE WITH INK

FIELD OF THE INVENTION

This invention relates generally to an identification machine for identification of articles and for the identification of the skin of animals or humans, and more specifically to a surgical instrument with a reciprocating needle for penetrating the surface of an article to apply ink or the like for identification or cosmetic surgery purposes.

In the past, the needle bar of identification machines were attached to the armature of the device by rubber bands or other precarious methods. The needle bars were hard to align and to keep secured. Also, there was no assurance against horizontal movement of the needle bar.

BACKGROUND OF THE INVENTION

Devices in the field of the present invention are used to place ink below the surface of an object or article. A pin or needle punctures the surface and places the ink below the surface. When the surface is the skin of a living being, and the ink does not react with the skin, the ink is placed at such a level in the skin, where it remains permanently. Because the ink is permanent, it is very important that the ink be applied very precisely. Correspondingly, it is very important that the position of the needle when it punctures the surface, can be precisely controlled. The needle must be moved back and forth in a reciprocating motion in order to puncture the surface, and this motion must be very limited in a direction perpendicular to the reciprocating motion.

U.S. Pat. No. 4,782,725 to Spaulding, describes an article identification device in the same field as the present invention, where the needle is reciprocated by an offset pin on the rotor of a motor. The offset pin is attached to an armature which slides in a slot. The needle is connected to the armature. In order to make the device light weight, the housing of the device, which defines the slot, and the armature are formed of a plastic. Due to the characteristics of plastic, tolerances between the armature and the slot in the housing have to be very large in order for the armature to slide easily in the slot. Plastic is also known to have a high thermal coefficient of expansion, such that the plastic expands and contracts greatly with temperature. Therefore, tolerances must be made extra large to compensate for expansion. The needle and armature oscillate in the reciprocating motion in the range of thousands of RPM or Hertz. Therefore, with continuous use, the plastic armature and slot receive much wear. This further increases the tolerance between the armature and the slot. While limiting movement of the needle in a plane perpendicular to the reciprocating motion is possible by the armature of Spaulding, it cannot be limited to more than the tolerance between the armature and the slot.

SUMMARY OF THE INVENTION

It is the object of the invention to provide a machine for applying indelible ink to the skin in a precise fashion for medical, veterinary and cosmetic purposes. In the medical area it can be used for marking the effected area of throat cancer while treatment is being done, this thereby indicating the location of the infection and also serving as an indication of the growth of the infection. The machine can also be used by dental surgeons for marking the gums of patients for future surgery. In the cosmetic field it can be used for applying permanent eye liner, permanent lip color or simply skin ornamentation. It is also useful during reconstruction of skin for burn victims. When skin is grafted from one portion of the body to another, it is not always the same color. Such areas as lips and the areola around the nipple can be normally colored when replaced with new skin. The veterinary field uses skin markings so as to mark animals for permanent identification to aid in research and animal management.

It is an object of the invention to provide precise application of indelible ink or the like to the skin of a human, or article using materials and electronic circuits in accordance with UL 544 (Underwriters Laboratory) standards.

It is another object of the invention to provide a lightweight easy and safe means for applying identifying markings for their various purposes. The machine, in accordance with the invention, with its attachments has exceptionally good balance, and can be operated with or without a foot switch from a power box or directly from a battery. The machine in accordance with the invention also has a jack plug which is located for connection with a lightweight power supply cord.

It is still another object of the invention to provide a means to apply identifying markings to objects without horizontal displacement so that better columnation of the needle bar and more precise application of the identification ink is achieved. Accordingly, it is the object of the invention to provide means to achieve this.

The present invention overcomes undesirable movement of the needle by providing guide bars and bushings that connect the armature to the housing. The guide bars slide in and out of the bushings when the armature reciprocates, and a material of the guide bars and bushings is such that tolerances can be much less than those between the armature and the housing. The armature and the housing can still be made of lightweight plastic in order to have the device weigh as little as possible. The guide bars and bushings can be made of metal to make them small and to contribute very light weight to the overall device. One guide bar and bushing can be placed on an end of the armature substantially opposite the needle. An armature bracket can be fastened to the housing after the armature is inserted in the track in order to fully or partially close off the open end of the track. Additional guide bars and bushings can then be placed between the armature and the armature bracket. If the armature bracket completely closes off the end of the track, the armature bracket can have a needle sleeve through which the needle passes. The material of the needle sleeve is made to allow tolerances between the needle sleeve and the needle which are less than the tolerances between the armature and the track. The armature bracket therefore provides support for an end of the armature which would otherwise be unsupported since without an armature bracket the end of the track is open.

Undesirable needle movements are also caused by vibration generated by the motor and transmitted through the housing. The entire device then vibrates in the hand of the operator and is difficult to accurately position the needle. In order to stabilize the needle, the present invention provides unique structure for mounting the motor. The motor is connected on only one side to the housing by bolts extending from a mounting wall inside the housing. In between the mounting wall and the motor is a damping plate and around the damping plate is a damping ring. The damping ring is positioned between, and contacts, the damping plate and the housing. The damping ring is formed of a material which absorbs and blocks vibrations. The damping plate can also be made of a material which absorbs and blocks vibrations.

All of these elements combine to form a needle stabilization means which very tightly limits undesirable movements of the needle and allows the needle to be very accurately positioned by the operator of the device.

A further object of the invention is to provide an identification device which is simple in design, rugged in construction and economical to manufacture.

For a better understanding of the invention and its operating advantages, reference is made to the accompanying drawings and descriptive matter in which preferred embodiments of the invention are illustrated.

DESCRIPTION OF PREFERRED EMBODIMENTS

Figure 1:
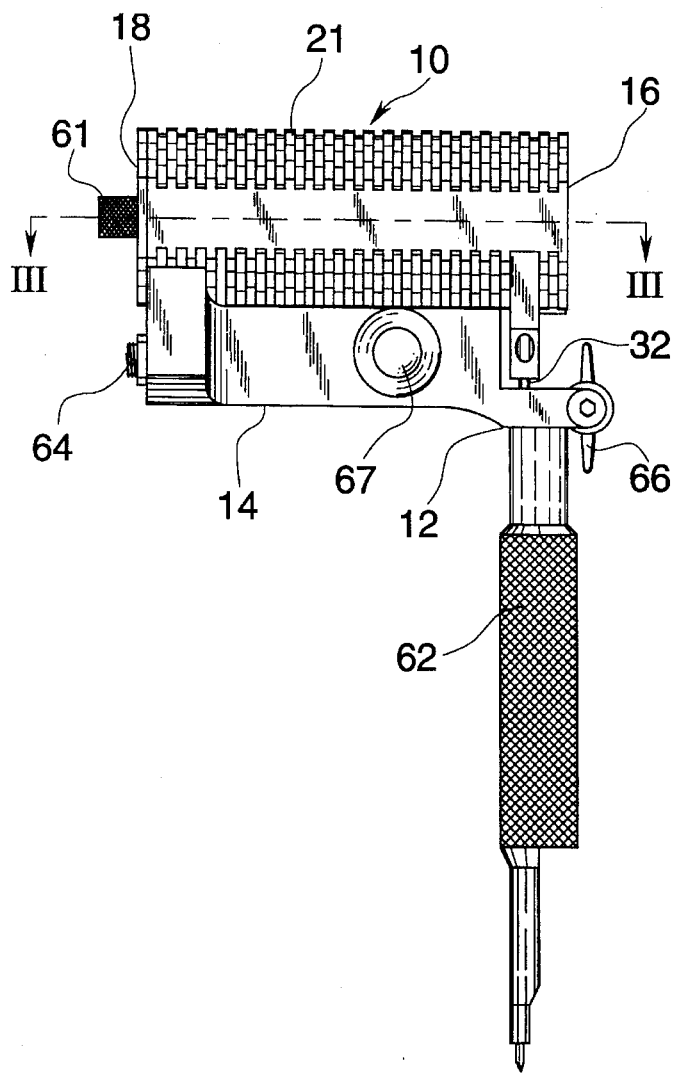
FIG. 1 is a side view of this invention emphasizing the variable speed control, and the armature bar.
Figure 3:
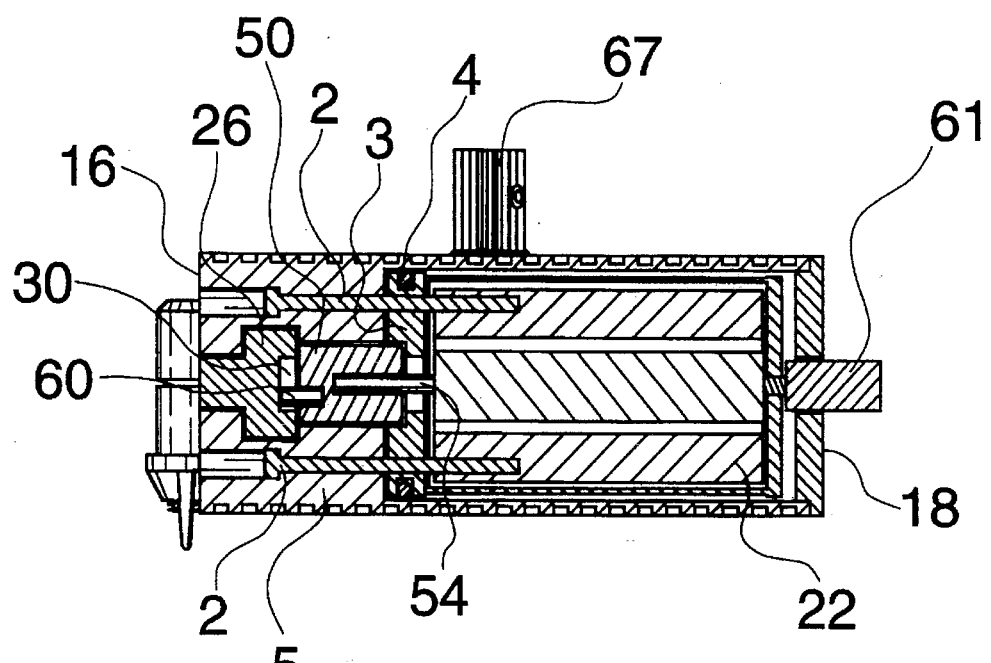
FIG. 3 is a top cross sectional view according to section lines III—III in FIGS. 1 and 2.
Figure 4:
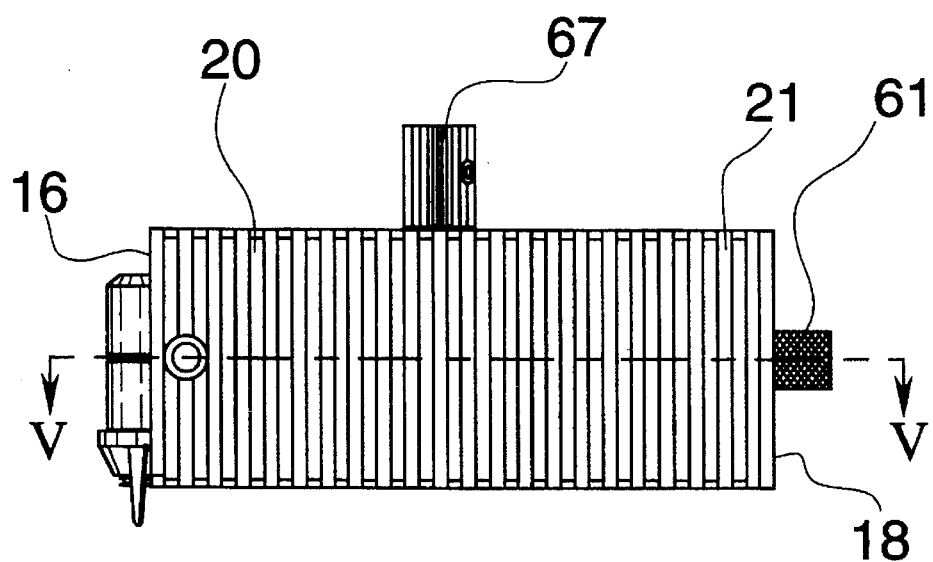
FIG. 4 is a top view of this invention.
Figures 5, 7:
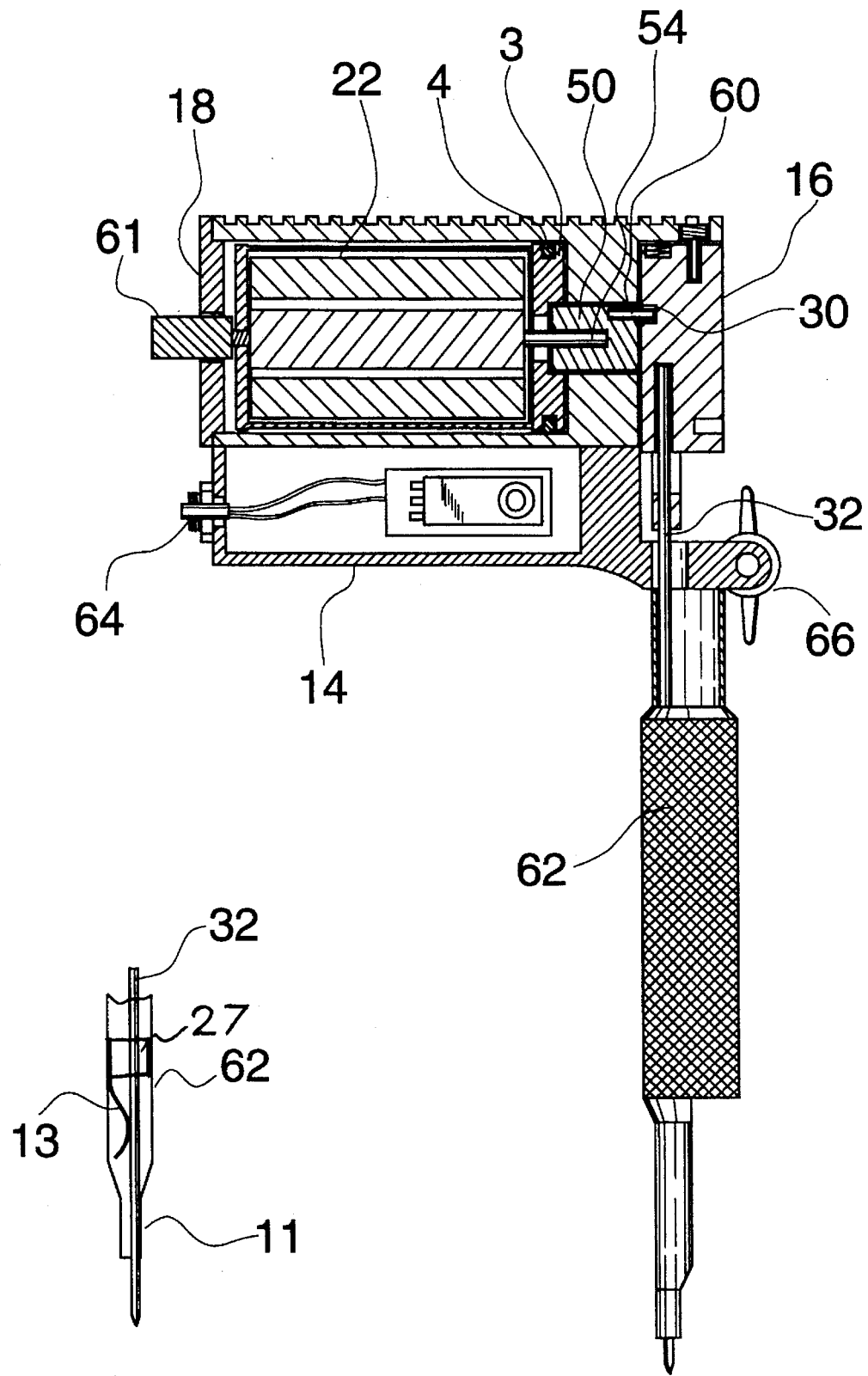
FIG. 5 is side cross sectional view according to section lines V—V in FIGS. 2 and 4.
FIG. 7 is a cross sectional view of the needle tube and the needle with a biasing means.
Figure 6:
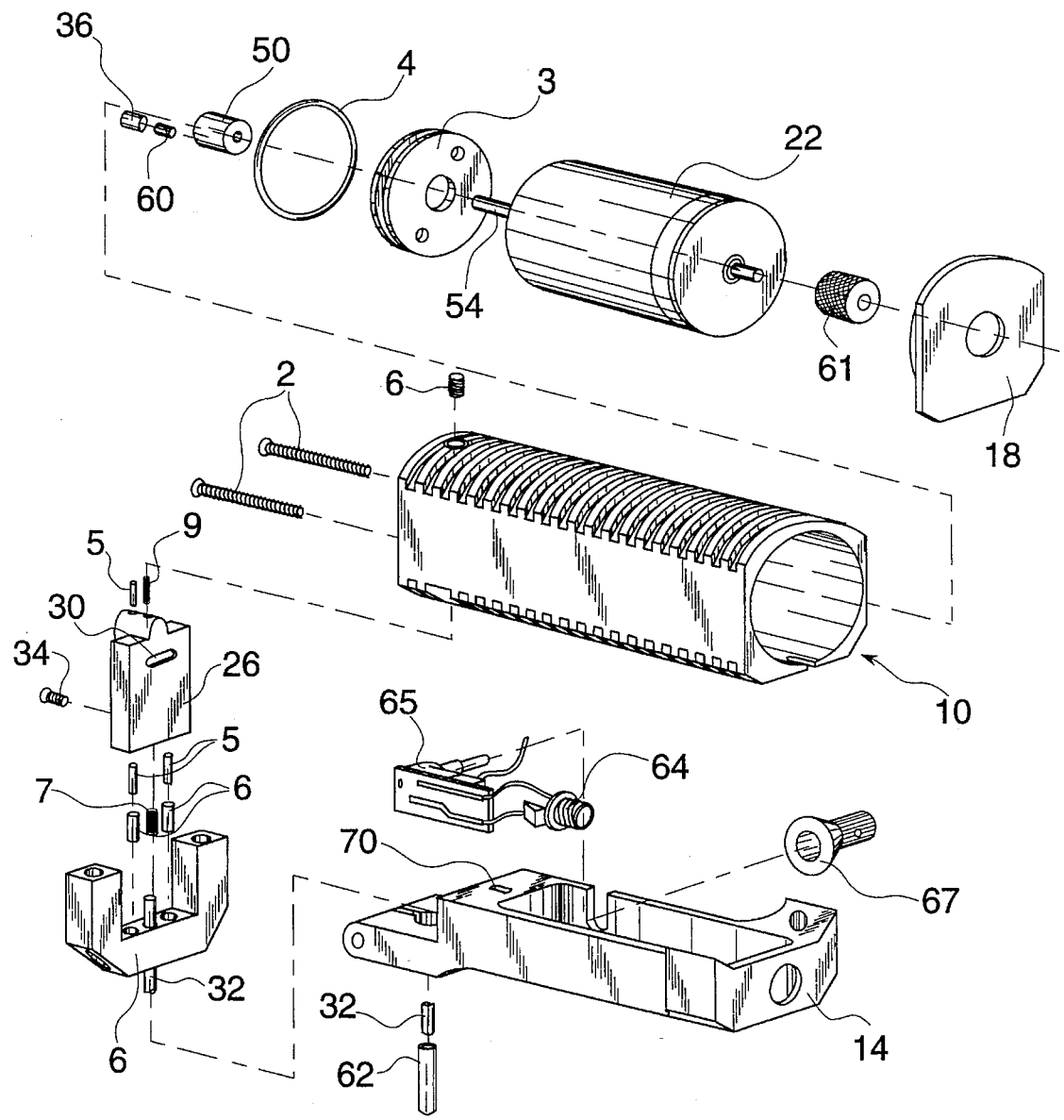
FIG. 6 is an exploded view of this invention.

The device according to the invention as seen in FIG. 1 includes a housing 10, preferably made of DELRIN for lightness and durability, including a needle guide portion 12, a bottom side portion or base 14, a front side portion 16, a rear portion 18. The housing 10 preferably includes fin like members 21 which are adapted to transfer heat to the exterior of the housing. Situated within the housing 10 there is advantageously arranged a motor 22 as seen in FIGS. 3, 5, 6 which preferably can run for 300 hours non-stop.

The motor 22 has been found to give off vibrations which can be transmitted through different paths to the needle. One of the paths for vibration is through the housing 10 which then causes the whole device to vibrate, and this prevents the hand of the operator holding the device, from holding the device steady and therefore holding the needle precisely. In order to stabilize the needle and limit its movements in plane perpendicular to the reciprocating direction of the needle, the present invention provides structure in the form of a needle stabilization means which removes or blocks vibration which is generated by the motor 22. As can be seen from FIGS. 3, 5 and 6, the motor is only supported in the housing on one side. The rest of the motor 22 is spaced from the housing 10. The housing 10 has a mounting wall mounted inside the housing. The mounting wall 20 defines bolt holes 1. Mounting bolts 2 extend from the mounting wall 20 towards the rear of the housing. A damping plate 3 is positioned between the mounting wall 20 and the motor 22. The mounting bolts 2 extend through the damping plate 3 and connect to the motor 22. The motor 22 is therefor supported in the front by the mounting wall 20 in a cantilever matter. Around the circumference of the damping plate 3 is a damping ring 4 which is positioned between the damping plate 3 and the housing 10. The damping ring is made of a material to absorb and block vibrations between the motor 22 and the housing 10. In a preferred embodiment, the damping ring 4 is an O-ring made of rubber and the damping plate 3 has a groove in its circumference for receiving the damping ring 4. Since the motor is only supported in the front, vibrations in the rest of the motor 22 will not be transmitted to the housing 10 and vibrations present in the front of the motor will be absorbed or blocked by the damping ring 4.

The dampening plate 3 can also be made of vibration absorbing material to absorb and block vibrations from the motor to the mounting wall 20. In the preferred embodiment, the mounting wall is integrally formed with the housing 10. The dampening ring absorbs and blocks vibration substantially perpendicular to an axis of rotation of the motor and the damping plate absorbs and blocks vibrations substantially parallel to an axis of rotation to the motor.

Figure 2:
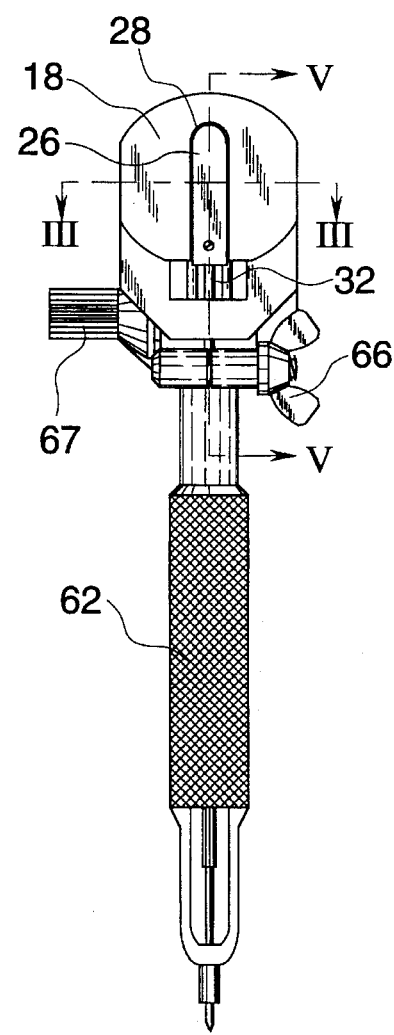
FIG. 2 is a front view showing the armature and needle.

An armature 26 is mounted within the housing 10 for upward and downward reciprocating movement, FIG. 2. The support member or armature 26, preferably has a dovetail or T-shape which is adapted to engage in a slotted or track portion 28 of the housing 10 as best seen in FIGS. 2 and 3. The needle stabilization means also includes guide bars 5 and guide bushings 8. These guide bars 5 and bushings 8 are positioned on the armature 26 and track 28. The guide bars 5 slide in and out of the slide bushings 8 during the reciprocating movement of the armature 26. The guide bars 5 and bushings 8 are made of a material which allows a smaller tolerance than the tolerance needed between the armature 26 and the track 28. The guide bars 5 and bushings 8 are preferably made of metal with the bushings being a low friction material such as impregnated bronze. In this way, tolerances that cause undesirable needle movement can be reduced while sill allowing the housing and armature to be formed of lightweight plastic material. Metal, such as stainless steel, guide bars 5 and bushings 8 can be relatively small and therefore contribute very little to the overall weight of the device. It is very important that the armature 26 can be light since it performs a reciprocating motion and must change direction several of thousands of times a second. In the embodiment shown in FIG. 8, a guide bar 5 and bushing 8 are positioned on one end of the armature 26 substantially opposite the needle 32. An armature bracket is positioned by an end of the track 28 and two other guide bars 5 and bushings 8 are positioned on the armature bracket 6 and the armature 26. The armature bracket 6 is a very important feature in that it allows an end of the track 28 to be at least partially closed off and provide a support for corresponding end of the armature 26. In a preferred embodiment, the armature bracket is removable by bolts to allow the armature to be inserted into the track 28 and then the armature bracket is installed. The armature bracket 6 can also completely close off the end of the track 28. The armature bar then defines a needle hole with a needle sleeve 7. The needle 32 passes through the needle sleeve 7. The needle sleeve 7 is made of a material which allows a tolerance between the needle and the needle sleeve 7 which is less in tolerance between the armature 26 and the track 28.

In a preferred embodiment, the guide bars 5 are mounted on the armature 26 and the guide bushing 8, which is opposite the needle, is mounted in the housing. The other two guide bushings 8 are mounted in the armature bracket 6 on opposite sides of the needle sleeve 7.

The guide bars 5 and bushings 8 are designed to have their minimum tolerances in a direction substantially perpendicular to reciprocating movements of the needle. The guide bar 5 and bushings 8 are formed of a material which wears less than the material of the armature and housing. The material of the guide bars 5 and bushings 8 also has a thermal coefficient of expansion less than the material of the housing 10 and armature 26.

The armature 26 advantageously includes a needle receiving bore for receiving needle 32. The bore is connected to locking means, generally designated 34. The locking means 34 includes a threaded screw engaging the armature 26 and this screw has a spring-loaded ball at the tip that engages a groove in the needle bar.

A cylindrical shaped needle tube 62 surrounds the needle 32 to act as protection for the needle 32 and also as a stationary grip by which to hold the device when applying ink to an article. The tube 62 fits into the circular needle guide portion 12 of the housing 10, as seen in FIG. 1. The needle tube 62 secured into place or removed by means of tightening or loosening of a nut 66 or a knurled knob.

It is also possible to have a rack and pinion connection between the needle tube 62 and the base. The rack gear will be mounted on needle 2 and the pinion gear would be rotatable on the base. Rotation of the pinion would then adjust the position of the needle tube relative to the base and the needle. The ease of rotatability of the pinion gear is set to hold the needle tube secure during normal operation of the tattoo machine, but allow the pinion gear to be movable by hand.

A crank means with a crank 50 is rotationally mounted within the housing 10 on a rotor 54 of the motor 22.

A crank pin 60 is mounted on a side of the crank 50 and is offset from a central axis of the crank 50. The pin 60 engages with the armature 26 through a crank slot 30 in the armature 26. The crank slot 30 is advantageously constructed so that upon rotation of the rotor 54 and crank 50, the crank pin 60, offset from the central axis, forces the armature 26 to reciprocate as the crank pin 60 follows a circular motion about, and spaced apart from, the central axis of the rotor 54. The horizontal crank slot 30 in the armature 26 allows a transmission of the rotational motion into the reciprocating motion of the armature 26. A sealed and lubricated armature bearing 36 is rotatably mounted on the crank pin, and the armature bearing and crank pin have a lower coefficient of friction and wear than between the crank pin 60 and the armature 26. Both the crank pin 60 and armature bearing 36 are inserted in the crank slot 30. The armature bearing 36 rolls back and forth in the crank slot 30 and also about the crank pin 60. In this way there is less friction and wear of the crank slot 30. There is also an armature spring 9 positioned between the housing 10 and the one end of the armature 26 opposite the needle 32. The armature spring 9 biases one side of the crank slot 30 against the armature bearing 36 and the crank pin 60. This further reduces any play or tolerance between the crank pin 60 and the armature 26.

Depending on the marking to be performed, the needle 32 can be of different diameters. Also when large areas are to be filled in with the same color, a plurality of needles is used. The needle tube 62 has an end 11 which is preferably neck down. Because of the different diameters of needles 32, and the possibility of using a plurality of needles, the internal diameter of end 11 must be large enough to accommodate the external diameter of the largest needle, or plurality of needles. Since the internal diameter of the end 11 will many times be larger than the external diameter of the needle 32, a large amount of play is present between the needle 32 and the needle tube 62, at the end 11. This play can cause wandering of the needle 32 and inaccurate placement or marking of the needle 32. In order to control wandering of the needle 32 at the end 11, a biasing means 13 is positioned in the needle tube 62 and applies a force to the needle 32 to bias the needle against one side of the needle tube 62 and in particular the end 11. The biasing means 13 is preferably formed by a leaf spring which has one end fastened to the needle tube 62 by a ring 27 which is expandable, and has the other end pressed against the needle 32. In this way, wandering of the needle 32 is greatly lessened, if not completely eliminated. The housing 10 also accommodates a motor shaft knob 61 for adjustment of the needle 32 when replacing the tube 62 in which the needle 32 is housed. Another feature of the needle stabilization means is forming the motor knob 61 and motor crank of a material, preferably brass, which is heavier than the material of the housing 10. In the preferred embodiment, the motor knob 61 is formed of a metal, preferably stainless steel. Since the motor knob 61 rotates with the motor, the additional mass smooths the rotation of the motor and causes the motor to generate less vibration.

A jack plug 64 is positioned below the motor shaft knob 61 on the rear portion of the housing 16 as seen in FIG. 1. A variable speed control 65 is built into the bottom of the machine housing. A speed control knob 67, preferably made of aluminum so as to also act as a heat sink, is located on the right side of the housing 10. Lastly, a slotted hole 70 is located on the bottom or base 14 for adjustment of the housing 10 to the base.

Figure 8:
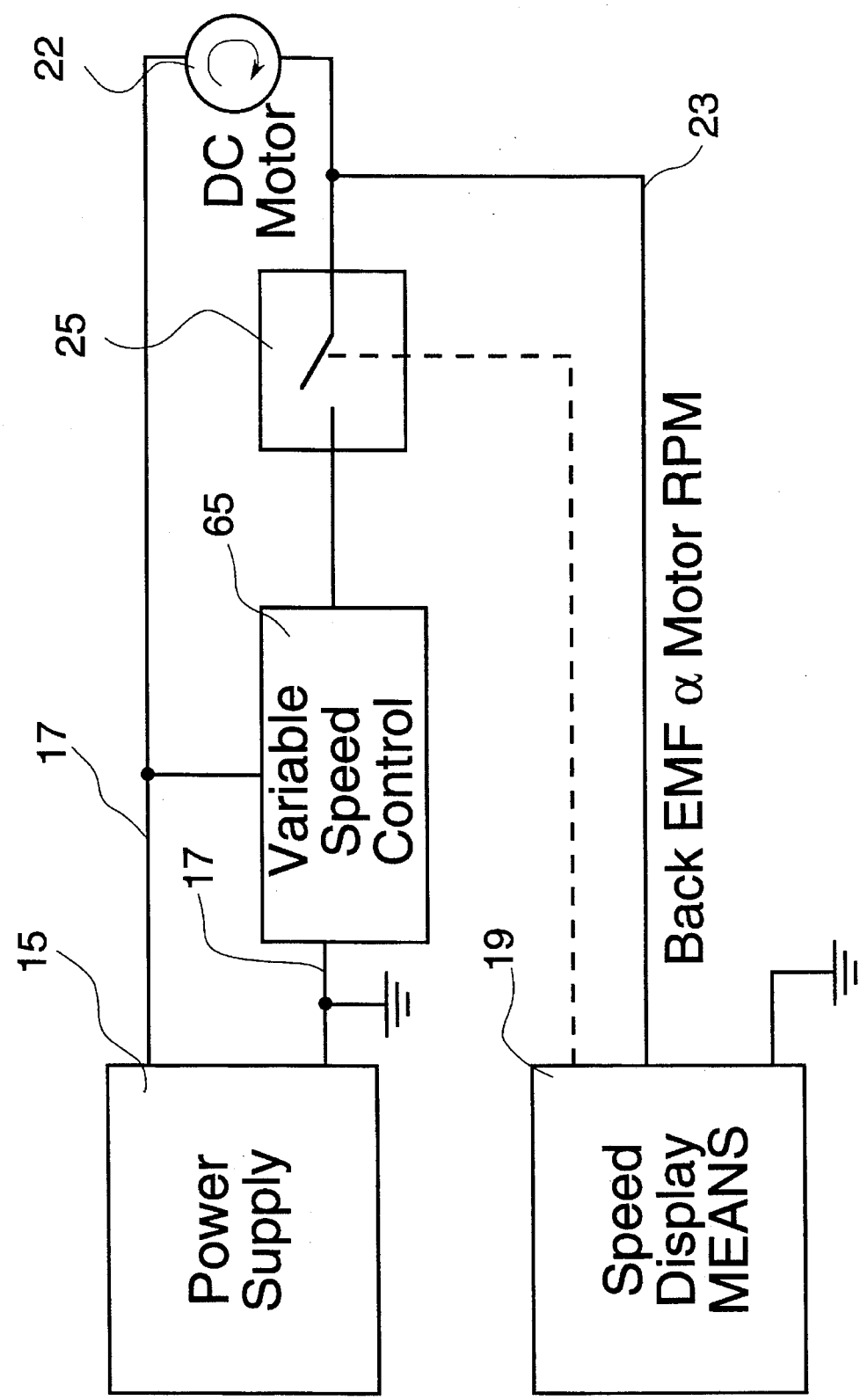
FIG. 8 is a circuit diagram showing how the speed of the needle is determined.

Due to natural resonances, and personal preferences of the operator, the speed at which the needle 32 oscillates is very important. If the needle oscillates too fast, harmonics can occur with the needle bouncing sideways uncontrollably. Therefore it is desirable to keep the oscillation speed of the needle below a maximum value. Also it is preferable to not have the needle oscillate too slowly because this will increase the time needed for marking. The present invention, as shown in FIG. 8 includes a speed display which shows the operator the speed or frequency that the needle 32 is oscillating. In FIG. 8, a power supply 15 sends power to the motor 22 over lines 17. The variable speed control 65 adjusts the speed based on the position of the speed control knob 67. The motor 22 is preferably a DC motor, and its speed will depend on the voltage, current of the power being fed to the motor, and the resistance applied to the turning of the motor. The present invention determines the speed of the motor by having a speed display means 19 which measures the back EMF of the motor 22 through a line 23. The speed display means 19 also cooperates with a chopper 25 which repetitively makes and breaks a connection between the motor 22 and the power supply 15. When the chopper connects the power supply to the motor, the motor is powered. When the chopper 25 disconnects the motor from the power supply, the armature of the motor still spins and turns the motor into a generator. The EMF (Electromotive Force) or voltage generated by the motor in this condition is proportional to the speed of the armature, and thus the needle. By measuring the back EMF when the chopper 25 is open, the speed display means can calculate the speed of the motor and the needle. The speed display means can have an indicator which indicates the speed to the operator.

This is important to the user due to the fact that different skin types and different locations on the body require additional needle speed to break the needle through the top layers of skin to inject the ink. The display allows for accurate settings for those above-mentioned situations.

As described above, the identification device of this invention makes it possible to use indelible ink either by dipping the needle in ink, having an automatic feed supply ink to the needle, or by a reservoir of ink in the tip of the needle to permanently mark objects or the skin of animals and humans with precision and ease. The identification device according to this invention has no horizontal displacement of the needle bar, all moving parts are self lubricating, and it weighs preferably less than 4.6 ounces with all its attachments.

While a specific embodiment of the invention has been shown and described in detail to illustrate the application of the principles of the invention, it will be understood that the invention may be embodied otherwise without departing from such principles.

What is claimed is:

1. A device for marking an article with ink, the device comprising;

a housing having a first end and a second end, said second end of said housing forming a track;

a motor mounted within said housing, said motor including a rotor;

an armature slidably positioned in said track of said housing;

crank means connected to said rotor and for converting rotary motion of said motor into reciprocating motion of said armature in said track;

a needle connected to said armature and reciprocating with said armature, said needle having means for inserting ink below a surface of the article;

needle stabilization means for limiting movements of said needle in a plane substantially perpendicular to said reciprocating motion of said needle caused by one of vibration of said motor and a tolerance between said armature and said track.

2. A device in accordance with claim 1, wherein:

said needle stabilization means limits movements of said needle caused by one of vibration of said motor and a tolerance between said armature and said track;

grip means are attached to said housing for providing a grip to a hand of an operator of the device;

said needle stabilization means limits said movements with respect to the hand of the operator.

3. A device in accordance with claim 1, wherein:

housing is formed of a light weight material;

said needle stabilization means includes a motor knob connected to said rotor on a side of said motor substantially opposite said crank means, said motor knob and crank means rotating with said rotor and being formed of a material heavier than said housing to smooth vibrations from said motor.

4. A device in accordance with claim 3, wherein:

said housing is plastic;

said motor knob extends out of said housing, is made of metal and has a grip surface for being rotated by the operator.

5. A device in accordance with claim 1, wherein:

said crank means includes a crank connected to said motor and rotatable by said motor, said crank having a crank pin spaced from an axis of rotation of said crank, said crank means also including an armature bearing rotatably mounted on said crank pin, said armature bearing and said crank pin having a lower coefficient of friction and wear than said crank pin and said armature;

said armature defining a crank slot, said armature bearing and said crank pin being slidably positioned in said crank slot for moving said armature in a reciprocating movement in said track by rotation of said crank;

said needle stabilization means including an armature spring means for biasing one side of said crank slot against said armature bearing;

said needle stabilization means also including a needle tube connected to said housing and surrounding said needle, said needle tube including a biasing means for biasing said needle against one side of said needle tube;

said needle stabilization means also includes a speed display means for displaying a speed of the needle;

said housing and said armature are formed of plastic.

6. A device in accordance with claim 1, wherein:

said crank means includes a crank connected to said motor and rotatable by said motor, said crank having a crank pin spaced from an axis of rotation of said crank, said crank means also including an armature bearing rotatably mounted on said crank pin, said armature bearing and said crank pin having a lower coefficient of friction and wear than said crank pin and said armature;

said armature defining a crank slot, said armature bearing and said crank pin being slidably positioned in said crank slot for moving said armature in a reciprocating movement in said track by rotation of said crank.

7. A device in accordance with claim 1, wherein:

said needle stabilization means including an armature spring means for biasing one side of said crank slot against said armature bearing.

8. A device in accordance with claim 1, wherein:

said needle stabilization means also including a needle tube connected to said housing and surrounding said needle, said needle tube including a biasing means for biasing said needle against one side of said needle tube.

9. A device in accordance with claim 1, wherein:

said needle stabilization means also includes a speed display means for displaying a speed of the needle.

10. A device for marking an article with ink, the device comprising;

a housing having a first end and a second end, said second end of said housing forming a track;

a motor mounted within said housing, said motor including a rotor;

an armature slidably positioned in said track of said housing;

crank means connected to said rotor and for converting rotary motion of said motor into reciprocating motion of said armature in said track;

a needle connected to said armature and reciprocating with said armature, said needle having means for inserting ink below a surface of the article;

needle stabilization means for limiting movements of said needle in a plane substantially perpendicular to said reciprocating motion of said needle, said needle stabilization means including a mounting wall attached to said housing, said needle stabilization means including a damping plate positioned between said mounting wall and said motor, said damping plate defining a bolt hole, said needle stabilization means including a bolt extending from said mounting wall through said bolt hole of said damping plate and into one side of said motor to only support said motor in said housing from said one side of said motor, said needle stabilization means including a damping ring positioned between said damping plate and said housing.

11. A device in accordance with claim 10, wherein:

said damping ring is made of vibration absorbing material to absorb and block vibrations from said motor to said housing.

12. A device in accordance with claim 11, wherein:

said damping ring is formed to absorb and block vibrations traveling substantially perpendicular to an axis of rotation of said motor.

13. A device in accordance with claim 10, wherein:

said damping plate is made of vibration absorbing material to absorb and block vibrations from said motor to said mounting wall.

14. A device in accordance with claim 13, wherein:

said damping plate is formed to absorb and block vibrations traveling substantially parallel to an axis of rotation of said motor.

15. A device in accordance with claim 10, wherein:

said mounting wall is integrally formed with said housing.

16. A device for marking an article with ink, the device comprising;

a housing having a first end and a second end, said second end of said housing forming a track;

a motor mounted within said housing, said motor including a rotor;

an armature slidably positioned in said track of said housing;

crank means connected to said rotor and for converting rotary motion of said motor into reciprocating motion of said armature in said track;

a needle connected to said armature and reciprocating with said armature, said needle having means for inserting ink below a surface of the article;

needle stabilization means for limiting movements of said needle in a plane substantially perpendicular to said reciprocating motion of said needle, said needle stabilization means includes a guide bar and bushing positioned on said armature and said track, said guide bar being slidable in said bushing during reciprocating movements of said armature, said guide bar and said bushing having a tolerance less than said tolerance between said armature and said track.

17. A device in accordance with claim 16, wherein:

said guide bar and bushing are positioned at one end of said armature and track, and another guide bar and bushing are positioned at another end of said armature and track.

18. A device in accordance with claim 17, wherein:

said needle stabilization means includes an armature bracket positioned on said housing across an end of said track adjacent said needle, said armature bracket including a needle sleeve through which said needle passes, said needle and said needle sleeve having a tolerance less than said tolerance between said armature and said track.

19. A device in accordance with claim 18, wherein:

said another guide bar and bushing are positioned on said armature and said armature bracket.

20. A device in accordance with claim 16, wherein:

said guide bar and bushing are positioned at an end of said armature and track substantially opposite said needle, and another two guide bars and bushings are positioned at an end of said armature and track with said needle.

21. A device in accordance with claim 20, wherein:

said two guide bars and bushings are positioned on opposite sides of said needle.

22. A device in accordance with claim 16, wherein:

said guide bar extends out of said armature and said guide bushing is positioned in said housing.

23. A device in accordance with claim 16, wherein:

said guide bar and bushing are formed of a material with a thermal coefficient of expansion less than said housing and said armature.

24. A device in accordance with claim 16, wherein:

said guide bar and said bushing having a tolerance in a direction perpendicular to said reciprocating movements of said needle less than a tolerance between said armature and said track in said direction perpendicular to said reciprocating movements of said needle.

\* \* \* \* \*